| United States Patent [19] | [11] Patent Number: 4,795,746 |
|---|---|
| Burgess et al. | [45] Date of Patent: Jan. 3, 1989 |

[54] SUBSTITUTED N-PHENYL-N'BENZOYL UREAS AND THEIR USE AS INSECTICIDES AND ACARICIDES

[75] Inventors: Michael J. Burgess; David P. Clifford, both of King's Lynn, England; Robert A. Sewell, Paulus Potterpad, Netherlands

[73] Assignee: The Dow Chemical Company, Midland, Mich.

[21] Appl. No.: 164,142

[22] Filed: Mar. 4, 1988

Related U.S. Application Data

[62] Division of Ser. No. 541,768, Oct. 13, 1983.

[30] Foreign Application Priority Data

Oct. 19, 1982 [GB] United Kingdom ............... 8229874

[51] Int. Cl.$^4$ ................. C07C 127/22; A01N 47/34
[52] U.S. Cl. ................................ 514/150; 534/850; 534/770
[58] Field of Search ............... 514/150; 534/770, 850; 564/44

[56] References Cited

U.S. PATENT DOCUMENTS 2,128,256  8/1938  Krzikalla et al. ............... 260/200
3,379,716  4/1968  Wallace et al. ............... 260/207.1
3,810,932  5/1974  Desai et al. ............... 260/465

FOREIGN PATENT DOCUMENTS 0175158  10/1982  Japan .
0188561  11/1982  Japan .

*Primary Examiner*—Glennon H. Hollrah
*Assistant Examiner*—Carolyn Greason
*Attorney, Agent, or Firm*—S. Preston Jones; Ronald G. Brookens

[57] ABSTRACT

Novel N-phenyl-N'benzoylureas which are useful as insecticides and acaricides.

1 Claim, No Drawings

SUBSTITUTED N-PHENYL-N'BENZOYL UREAS AND THEIR USE AS INSECTICIDES AND ACARICIDES

CROSS-REFERENCE TO RELATED APPLICATION

This is a divisional of application Ser. No. 541,768, filed Oct. 13, 1983.

BACKGROUND OF THE INVENTION

The present invention relates to certain N-phenyl-N'-benzoylureas, to a process for their preparation and to their use as arthropodicides, especially as insecticides and acaricides.

The invention provides, as new compounds, the N-phenyl-N'benzoylureas of the general formula

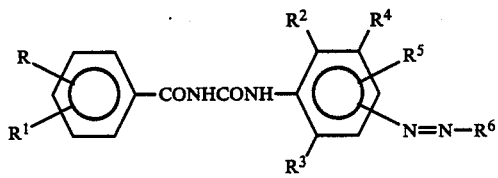

wherein R and $R^1$ are each independently a hydrogen or halogen atom, a $C_1$-$C_4$ alkyl or a $C_1$-$C_4$ haloalkyl group; $R^2$ and $R^3$ are each independently a hydrogen or halogen atom or a $C_1$-$C_4$ alkyl group; $R^4$ and $R^5$ are each independently a hydrogen or halogen atom, or a $C_1$-$C_4$ alkyl, $C_1$-$C_4$ haloalkyl, $C_1$-$C_4$ alkoxy, $C_1$-$C_4$ haloalkoxy, $C_2$-$C_4$ alkenyl, $C_2$-$C_4$ haloalkenyl, $C_2$-$C_4$ alkenyloxy, $C_2$-$C_4$ haloalkenyloxy or a $C_2$-$C_4$ alkynyl group; $R^6$ is

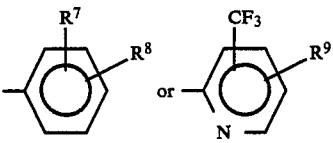

wherein $R^7$ and $R^8$ are each independently a hydrogen or halogen atom, or a nitro, $C_1$-$C_4$ alkyl, $C_1$-$C_4$ haloalkyl or cyano group and $R^9$ is a halogen atom or a $C_1$-$C_4$ alkyl or a $C_1$-$C_4$ haloalkyl group.

The present invention also provides processes for the preparation of the benzoylureas of formula I.

In the present specification and claims, the terms halo, halogen, or the term halo as it is employed in haloalkyl, haloalkoxy, haloalkenyl or haloalkenyloxy designates bromo, chloro or fluoro.

In the present specification and claims the terms alkyl, haloalkyl, alkoxy, haloalkoxy designate straight-chained radicals of 1 to 4 carbon atoms or branched-chained or cyclic radicals of 3 or 4 carbon atoms; the terms alkenyl, haloalkenyl, alkenyloxy or haloalkenyloxy designates straight-chained radicals of 2 to 4 carbon atoms or branched-chained radicals of 3 or 4 carbon atoms; the term alkyl designates straight-chain radicals of 2 to 4 carbon atoms or a branched-chained radical of 4 carbon atoms.

In the first of these processes, process (a), a phenylazoaniline of the general formula:

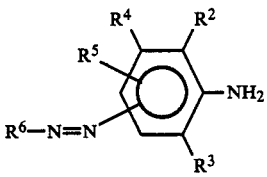

wherein $R^2$, $R^3$, $R^4$, $R^5$ and $R^6$ are as defined above is reacted with a benzoylisocyanate of the general formula

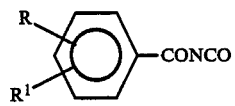

wherein R and $R^1$ are as above defined in the presence of an appropriate solvent.

In the second of these processes, process (b) a 4-arylazophenylisocyanate of the general formula

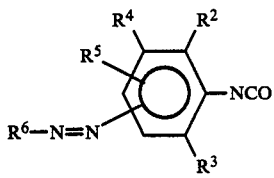

wherein $R^2$, $R^3$, $R^4$, $R^5$ and $R^6$ are as above defined is reacted with a benzamide of the formula

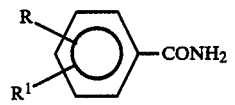

wherein R and $R^1$ are as above defined in the presence of an appropriate solvent.

Employing 4-phenylazoaniline and 2,6-difluorobenzoylisocyanate as the starting materials, the reaction scheme of process (a) is set forth below along with the reaction scheme for process variant (b) wherein 4-phenylazophenylisocyanate and 2,6-difluorobenzamide are employed as the starting materials.

Reaction Scheme (a)

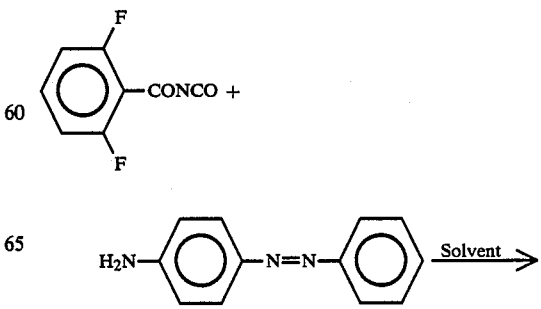

-continued

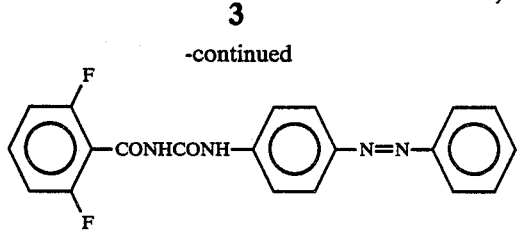

Reaction Scheme (b)

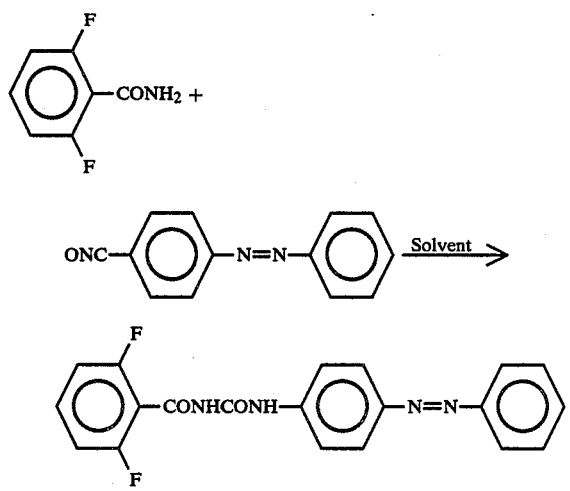

As indicated above, the processes for the preparation of the compounds of the invention are preferably carried out in the presence of suitable solvents and diluents. The particular solvent employed is not critical as practically all inert organic solvents can be used for this purpose, especially aliphatic and aromatic hydrocarbons and chlorinated hydrocarbons; additionally, ethers, ketones and nitriles can be employed.

The reaction temperature may be varied within a fairly wide range and can include reflux conditions. In general the reaction is carried out at a temperature in the range of from 0° to 130° C., preferably at room temperature. The reaction preferably takes place at atmospheric pressure.

In carrying out these above processes, the reactants are preferably employed in equimolar amounts.

The compounds of the present invention are normally crystalline solids having a low solubility in water and having a moderate solubility in many organic solvents. The componds have low phytotoxicity and have exceptional activity in the control of various undesirable agricultural, household and veterinary insect pests.

Examples of the various insects which can be controlled by the active compounds of the present invention are members of the orders Lepidoptera, Coleoprtera, Diptera, Orthoptera, Homoptera, Thysanoptera and Acarina. They are active against normally sensitive and resistant species at some stages of development. Examples of insect pests comprising the above include the tobacco budworm (*Heliothis virescens*), the beet armyworm (*Spodoptera exigua*), the Egyptian cotton leafworm (*Spodoptera littoralis*), the American bollworm (*Heliothis armigera*), the diamond-back moth (*Plutella maculipennis*), the gypsy moth (*Lymantria dispar*), the cutworm (*Agrotis segetum*), the Mediterranean flour moth (*Ephestia keuhniella*), the Colorado potato beetle (*Leptinotarsa decimlineata*), the mustard beetle (*Phaedon cocheariae*), the cotton boll weevil (*Anthomomus grandis*, the Mexican bean beetle (*Epilachna varivestis*), the khapra beetle (*Trogoderma granarium*), the housefly (*Musca domestica*), the lesser housefly (*Fannia canicularis*), the Mediterranean fruit fly (*Ceratitis capitata*), the black blow fly (*Phormia regina*), the cabbage rootfly (*Hylemya brassicae*), the yellow fever mosquito (*Aedes aegypti*), the malaria mosquito (*Anopheles stephensi*), the desert locust (*Schistocerca gregaria*), the migratory locust (*Locusta migratoria*), the German cockroach (*Blattella germanica*), the American cockroach (*Periplaneta americana*), the pear psylla (*Psylla pyricola*), the onion thrips (*Thrips tabaci*), and the citrus rust mite (*Phyllocoptruta oleivora*).

The compounds of the present invention are highly active and can be employed to kill insects outright and/or to prevent adult emergence from the juvenile forms of the insect. In such applications, the insect to be controlled and/or its habitat is contacted or treated with an insecticidal amount of one or more of the compounds of the present invention. The compounds may be administered orally to warm blooded animals from which they are excreted unchanged and they effectively combat the larvae of certain insects which inhabit faeces, e.g., the face fly, horn fly and buffalo fly.

For all such uses, the compounds of the present invention can be employed in unmodified form. However, the present invention also includes within its scope the use of an insecticidally-effective amount of the active ingredient in composition form with a material known in the art as a diluent or carrier.

Thus, for example, compositions employing one or a combination of these active ingredients can be in the form of a liquid or a dust, and the adjuvant employed can be any one of a plurality of materials including aromatic solvents, petroleum distillates, water or other liquid carriers, propellant substances, surface-active dispersing agents, light absorbers and finely-divided carrier solids.

The exact concentration of one or a combination of the compounds of the present invention in a composition thereof with an adjuvant therefore can vary; it is only necessary that one or a combination of the compounds be present in a sufficient amount so as to make possible the application of an insecticidally-effective or inactivating dosage.

Generally, for practical applications, one or a combination of these active ingredients can be broadly applied to the insect larvae or their habitat in compositions containing from 0.0001 to 98 percent by weight, preferably 5 to 50 percent by weight, of the compounds.

The compounds of the present invention or compositions containing them can advantageously be employed in combination with one or more additional pesticidal compounds. Such additional pesticidal compounds may be insecticides, nematocides, acaricides, herbicides, fungicides or bactericides which are compatible with the compounds of the present invention in the medium selected for application and not antagonistic to the activity of compounds. Accordingly, in such embodiments, the pesticidal compound is employed as a supplemental toxicant for the same or for a different pesticidal use, or as an additive. The compounds used in combination which the compounds of the invention are generally present in a ratio from 1 to 100 parts of the compound of the present invention to form 100 to 1 parts of the additional compound(s).

The compounds of this invention are, or tend to be, slow acting, i.e., they disrupt the molting of the insect, thereby killing it. As a result, some time can pass before the insects are killed. Accordingly, an increased benefit can be obtained by combining the compounds of this invention with quicker acting insecticides such as, for example, organophosphorus compounds, carbamates and pyrethroids. Because of this different mode of action, the compounds of this invention kill or control the more common insecticides and thus they inhibit or delay the development of resistance to such insecticides.

The present invention will be further illustrated with reference to the following Examples.

EXAMPLE 1

The preparation of N-(2,6-difluorobenzoyl)-N'-(4-phenylazophenyl)-urea

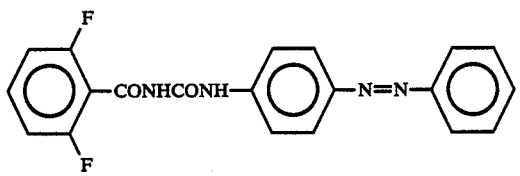

(a) Under room temperature conditions a solution of 3.98 grams (g) (0.017 mol) of 4-phenylazoaniline hydrochloride in 50 milliliters (ml) of water was neutralized with an excess of concentrated ammonia and then extracted twice with 25 ml portions of toluene. The organic extracts were thoroughly washed twice with 50 ml portions of water and then dried over anhydrous sodium sulphate. The toluene solution was then added to a stirred solution of 3.42 g (0.0187 mol) of 2,6-difluorobenzoylisocyanate in 3.5 mls of toluene. The resulting precipitate was filtered and washed first with chilled toluene and then petroleum ether. Yield of above-identified product 5.64 g, 87% of theory, m.p. 241°–243° C. (Compound No. 1).

Calculated for $C_{20}H_{14}F_2N_4O_2$. Found: C=63.23; H=3.69; N=14.70. Theory: C=63.16; H=3.71; N=14.73.

(b) A mixture of 23.37 g (0.1 m) of 4-phenylazoaniline and 14.84 g (0.075 m) of trichloromethyl chloroformate in 100 ml of 1,4-dioxan was heated with stirring under reflux conditions for 4 hours. The solvent and excess trichloromethyl chloroformate were distilled off under atmospheric pressure up to a maximum pot temperature of 130° C. The resultant crude isocyanate, an oil, was diluted with a mixture of 15.71 g (0.1 m) of 2,6-difluorobenzamide in 100 ml of toluene. The mixture was stirred under reflux for one and one-half (1.5 hours). The reaction mixture was cooled and the solid which precipitated was collected by filtration and washed with chilled toluene and then petroleum ether (both at 40°–60° C.). The crude solid was recrystallized from methyl ethyl ketone to yield 22.7 g (60% of theoretical) of the above-named product, as an orange crystalline solid. The product melted at 241°–242° C. (Compound No. 1).

Calculated for $C_{20}H_{14}F_2N_4O_2$. Found: C=63.39; H=3.73; N=14.82. Theory: C=63.16; H=3.71; N=14.73.

By following the preparative procedures as set forth hereinabove, the following compounds can be prepared.

TABLE 1

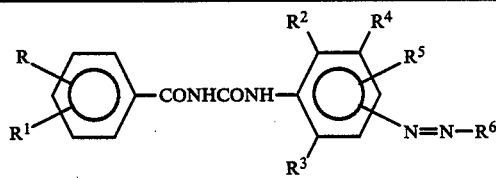

| Compound Number | R | $R^1$ | $R^2$ | $R^3$ | $R^4$ | $R^5$ | $R^{6*}$ | Ring Position —N=N— | Melting Point °C. |
|---|---|---|---|---|---|---|---|---|---|
| 2 | H | H | H | H | $CH_3$ | 3-$CH_3$ | Ph | 4 | 231–233 |
| 3 | 2-Cl | H | H | H | $CH_3$ | 3-$CH_3$ | Ph | 4 | 211–214 |
| 4 | 2-Cl | H | H | H | $CH_3$ | H | Ph | 4 | 222–225 |
| 5 | 2-Cl | H | $CH_3$ | H | H | H | Ph(2-$CH_3$) | 4 | 212–215 |
| 6 | 2-F | H | H | H | $CH_3$ | 3-$CH_3$ | Ph | 4 | 185 |
| 7 | 3-$CH_3$ | H | H | H | $CH_3$ | 3-$CH_3$ | Ph | 4 | 210–211 |
| 8 | 2-F | 6-F | H | H | $CH_3$ | 3-$CH_3$ | Ph | 4 | 208–210 |
| 9 | 3-Cl | H | H | H | $CH_3$ | 3-$CH_3$ | Ph | 4 | 205–206 |
| 10 | 2-$CH_3$ | 6-$CH_3$ | H | H | $CH_3$ | 3-$CH_3$ | Ph | 4 | 212 |
| 11 | 2-n-$C_4H_9$ | 6-n-$C_4H_9$ | n-$C_4H_9$ | n-$C_4H_9$ | O—n-C—$C_4H_9$ | 3-O—n-$C_4H_9$ | 2-Py(3-$CF_3$, 5-$CH_3$) | 4 | |
| 12 | 3-$CF_3$ | H | H | H | $CH_3$ | 3-$CH_3$ | Ph | 4 | 218 |
| 13 | 4-Cl | H | H | H | $CH_3$ | 3-$CH_3$ | Ph | 4 | 265 |
| 14 | H | H | H | H | $CH_3$ | 4-$CH_3$ | Ph | 3 | |
| 15 | 3-$CF_3$ | 5-$CF_3$ | F | $CH_3$ | $OCF_3$ | 4-C(F):$CF_2$ | 2-Py(3,5-$CF_3$)$_2$ | 5 | |
| 16 | 4-Cl | — | $CH_3$ | H | H | H | Ph(2-$CH_3$) | 4 | 270–273 |
| 17 | 2-Cl | 6-Cl | $CH_3$ | H | H | H | Ph(2-$CH_3$) | 4 | 208–210 |
| 18 | 2-F | H | $CH_3$ | H | H | H | Ph(2-$CH_3$) | 4 | 204–205 |
| 19 | 2-F | 6-F | H | H | $CH_3$ | H | Ph | 4 | 211–213 |
| 20 | 2-F | 6-F | H | H | $CH_3$ | H | Ph(4-$NO_2$) | 4 | 267–271 |
| 21 | 2-$CF_3$ | H | H | H | $CH_3$ | 3-$CH_3$ | Ph | 4 | 207 |
| 22 | 2-Cl | 6-Cl | H | H | $CH_3$ | 3-$CH_3$ | Ph | 4 | 250 |
| 23 | 2-F | 6-F | H | H | $CH_3$ | 3-$CH_3$ | Ph(3-$NO_2$) | 4 | 231–234 |
| 24 | 4-$C_2F_5$ | 6-F | Cl | Cl | Cl | 4-$OCF_3$ | Ph(3-CN) | 3 | |
| 25 | 2-Br | 3-F | | F | —OCH:$CHCH_3$ | 4-C:CH | Ph(3-n-$C_4H_9$) | 3 | |
| 26 | 2-F | 6-F | H | H | H | H | Ph(4-$NO_2$) | 4 | 247–251 |
| 27 | 2-F | 6-F | H | H | $CH_3$ | 3-$CH_3$ | Ph(3,5-($CH_3$)$_2$) | 4 | 210–213 |
| 28 | 2-$CH_3$ | H | H | H | $CH_3$ | 3-$CH_3$ | Ph | 4 | 216 |
| 29 | 2-F | 6-F | H | H | $CH_3$ | H | Ph(4-Cl) | 4 | 240–242 |

TABLE 1-continued

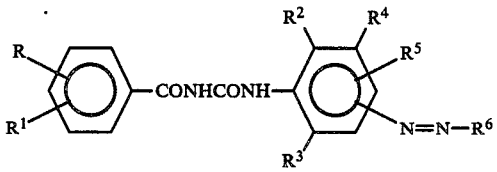

| Compound Number | R | $R^1$ | $R^2$ | $R^3$ | $R^4$ | $R^5$ | $R^{6*}$ | Ring Position —N=N— | Melting Point °C. |
|---|---|---|---|---|---|---|---|---|---|
| 30 | 2-F | 6-F | H | H | $CH_3$ | H | Ph(4-$NO_2$) | 4 | 240-243 |
| 31 | 2-F | 6-F | H | H | $CH_3$ | 3-$CH_3$ | Ph(4-$NO_2$) | 4 | 230-234 |
| 32 | 2-F | 6-F | $CH_3$ | H | H | H | Ph(2-$CH_3$) | 4 | 206-208 |
| 33 | 2-F | 6-F | H | H | $CH_3$ | 3-$CH_3$ | Ph(4-Cl) | 4 | 240-244 |
| 34 | 2-$CH_3$ | H | $CH_3$ | H | H | H | Ph(2-$CH_3$) | 4 | 232-234 |
| 35 | 3-$CH_3$ | H | $CH_3$ | H | H | H | Ph(2-$CH_3$) | 4 | 335-337 |
| 36 | 2-F | 6-F | H | H | F | H | Ph(4-$CF_3$) | 4 | 256-259 |
| 37 | 2-F | H | H | H | F | H | Ph(4-$CF_3$) | 4 | 229-231 |
| 38 | 2-F | H | H | H | $CH_3$ | H | Ph(4-$NO_2$) | 4 | 272-277 |
| 39 | 2-F | H | H | H | $CH_3$ | H | Ph | 4 | 182-185 |
| 40 | 2-Cl | 6-Cl | $CH_3$ | H | $CH_3$ | H | Ph | 4 | 256-257 |
| 41 | 2-F | 6-F | H | H | H | H | Ph | 3 | 188-190 |
| 42 | 2-Cl | H | H | H | $CH_3$ | H | Ph(4-$NO_2$) | 4 | 245-247 |
| 43 | 2-F | H | $CH_3$ | H | H | 3-$CH_3$ | Ph | 4 | 208-209 |
| 44 | 2-F | H | H | H | $CH_3$ | 3-$CH_3$ | Ph(4-$NO_2$) | 4 | 189-194 |
| 45 | 2-F | H | H | H | Cl | H | Ph(4-$NO_2$) | 4 | 285-289 |
| 46 | 2-F | 6-F | H | H | $OCH_3$ | H | Ph(2,4-$F_2$) | 4 | 219-222 |
| 47 | 2-F | 6-F | $CH_3$ | H | $CH_3$ | H | Ph | 4 | 247-248 |
| 48 | 2-F | 6-F | H | H | $CH_3$ | $CH_3$ | Ph(4-Cl,2-$CF_3$) | 4 | 236-239 |
| 49 | 2-F | H | $CH_3$ | H | $CH_3$ | H | Ph | 4 | 212-214 |
| 50 | 2-F | 6-F | $CH_3$ | H | H | 3-$CH_3$ | Ph | 4 | 201-202 |
| 51 | 2-F | 6-F | F | H | H | H | Ph | 3 | 216-218 |
| 52 | 2-F | 6-F | F | H | H | H | Py | 3 | |
| 53 | 2-Cl | H | $CH_3$ | H | $CH_3$ | H | Ph | 4 | 214-215 |
| 54 | 2-Cl | H | H | H | $CH_3$ | 3-$CH_3$ | Ph(4-$NO_2$) | 4 | 256-259 |
| 55 | 2-$CH_3$ | H | $CH_3$ | H | $CH_3$ | H | Ph | 4 | 221-226 |
| 56 | 2-Cl | H | H | H | H | H | Ph | 3 | 192-194 |
| 57 | 4-$CH_3$ | H | H | H | $CH_3$ | 3-$CH_3$ | Ph | 4 | |
| 58 | 2-Cl | H | H | H | H | H | Ph | 4 | 270-271 |
| 59 | H | H | H | H | H | H | Ph | 5 | 208-211 |
| 60 | 2-F | 6-F | H | H | $OCF_2CHCl_2$ | H | Ph | 4 | 220-221 |
| 61 | 2-F | 6-F | H | H | $OCF_2CHCl_2$ | H | Ph(4-$NO_2$) | 4 | 249 |
| 62 | 2-Cl | 6-Cl | $CH_3$ | H | H | $CH_3$ | Ph | 4 | 179-180 |
| 63 | 2-Cl | H | H | H | $OCH_3$ | H | Ph(2,4-$F_2$) | 4 | 206-208 |
| 64 | 2-Cl | H | Br | Br | H | H | Ph | 4 | 214-216 |
| 65 | 2-Cl | H | H | H | F | F | Ph(4-$CF_3$) | 4 | 213-216 |
| 66 | 2-F | H | $CH_3$ | $CH_3$ | H | H | Ph | 4 | 196-197 |
| 67 | 2-F | H | H | H | H | H | Ph | 4 | 225-227 |
| 68 | 2-$CH_3$ | H | H | H | H | H | Ph | 4 | 245-247 |
| 69 | 2-Cl | H | H | H | $CH_3$ | $CH_3$ | Ph(2-$CF_3$, 4-Cl) | 4 | 219-220 |
| 70 | 2-Cl | H | H | H | $CH_3$ | $CH_3$ | Ph(2-CN, 4-Cl) | 4 | 250 |
| 71 | 2-F | H | H | H | $OCH_3$ | H | Ph(2,4-$F_2$) | 4 | 218-220 |
| 72 | 2-F | H | Br | Br | H | H | Ph | 4 | 205-207 |
| 73 | 2-F | H | H | H | F | F | Ph(4-$CF_3$) | 4 | 229-230 |
| 74 | 2-F | H | H | H | $CH_3$ | $CH_3$ | Ph(2-$CF_3$, 4-Cl) | 4 | 222-224 |
| 75 | 2-F | H | $CH_3$ | $CH_3$ | H | H | Ph | 4 | 170-172 |
| 76 | 4-$CH_3$ | H | H | H | H | H | Ph | 4 | 285-286 |
| 77 | 2-$CH_3$ | H | Br | Br | H | H | Ph | 4 | 220-222 |
| 78 | 2-$CH_3$ | H | H | H | F | F | Ph(4-$CF_3$) | 4 | 247-249 |
| 79 | 2-F | H | H | H | $CH_3$ | $CH_3$ | Ph(3-$NO_2$, 4-Cl) | 4 | 258-261 |
| 80 | 2-F | 6-F | H | H | $CH_3$ | $CH_3$ | Ph(2-CN, 4-Cl) | 4 | 259-261 |
| 81 | 2-F | 6-F | Br | Br | H | H | Ph | 4 | 224-225 |
| 82 | 2-F | 6-F | F | H | H | F | Ph(4-$CF_3$) | 4 | 217-219 |
| 83 | 2-F | 6-F | H | H | F | F | Ph(4-$CF_3$) | 4 | 253-254 |
| 84 | 2-F | 6-F | H | H | $CH_3$ | $CH_3$ | Ph(4-Cl, 3-$NO_2$) | 4 | 264-266 |
| 85 | 2-F | H | H | H | H | H | Ph | 5 | 195-197 |
| 86 | 2-Cl | 6-Cl | H | H | $CH_3$ | $CH_3$ | Ph(4-Cl, 3-$NO_2$) | 4 | 251-255 |
| 87 | 2-Cl | 6-Cl | Br | Br | H | H | Ph | 4 | 220-222 |
| 88 | 2-F | 6-F | H | H | F | F | Ph | 4 | 227-228 |
| 89 | 2-Cl | 6-Cl | H | H | F | F | Ph(4-$CF_3$) | 4 | 233-234 |
| 90 | 2-$CH_3$ | H | $CH_3$ | H | H | $CH_3$ | Ph | 4 | 231-234 |

*Ph = Phenyl
Py = Pyridyl

EXAMPLE 2

Cotton plants were grown to four true leaves of 7-8 cm diameter. The test compound was prepared as an aqueous/acetone solution or suspension at the required concentration. The foliar parts of the cotton plant were dipped in the test medium for a 10 second period. After drying they were kept in a glasshouse at a temperature of 20° to 25° C. with a minimum photoperiod of 12 hours.

Individual leaves from each treatment were removed and placed in separate 9 cm diameter plastic petri dishes where they were infested with ten, 3rd instar larvae of *Spodoptera littorallis*. The experimental units were kept in an environmental room at 25° C., 70% humidity with a photoperiod of 16 hours. The leaves in each unit were replaced daily with leaves from plants of the same treatment, i.e., 0, 1, 2 and 3 days.

Assessment was made on the fourth day as a comparison of treated with untreated controls and expressed as a percentage mortality on a scale of 1 to 5 where 1=90-100% mortality
2=75-89% mortality
3=50-74% mortality
4=25-49% mortality and
5=0-24% mortality.

The results of this assessment showed that at a treating dosage of 400 milligrams of the active compound per liter (mg/l), each of compounds 1, 2, 3, 4, 5, 6, 8, 10, 12, 17, 18, 19, 23, 26, 27, 28, 30, 31, 32, 33, 36, 37, 38, 39, 41, 42, 43, 44, 46, 47, 48, 49, 50, 51, 53, 54, 56, 70 and 81 gave a scale rating of 1. Compounds 7, 21, 22, 40 and 57 gave a scale rating of 2; compounds 16 and 64 gave a scale rating of 3; compounds 34 and 45 gave a scale rating of 4 and compounds 9, 13, 20 and 35 gave a scale rating of 5. In addition, this assessment showed that at a treating dosage of 10 mg/l, each of compounds 2, 3, 4, 5, 6, 8, 10, 19, 23, 27, 28, 32, 33, 36, 37, 39, 41, 42, 43, 44, 46, 47, 48, 49, 50, 51, 53 and 56 gave a scale rate of 1; compounds 18 and 54 gave a scale rating of 2; compounds 1, 16 and 57 gave a scale rating of 3; compound 187 gave a scale rating of 4 and each of compounds 7, 9, 12, 13, 20, 21, 22, 26, 30, 31, 34, 35, 38, 40, 45, 64, 70 and 81 gave a scale rating of 5.

EXAMPLE 3

One day old eggs of high viability were obtained from Egyptian cotton leafworm adults (*Spodoptera littoralis*) at the optimum egg laying time. The adults (moths) had laid the eggs on blotting paper cylinders from which suitable egg masses containing approximately 200 eggs were taken. The upper layers of eggs are removed by brashing until the egg mass was reduced to a single layer. Each egg mass was divided into two halves and each half was taped onto microscope slides using double sided tape. One half of the egg mass was left untreated to serve as a control and the other half was treated as follows:

The test compound was prepared as an aqueous acetone dispersion at the required concentration. The egg mass was dipped for a 3 second period into the test solution at the desired concentration. The treated and untreated eggs were kept in an incubator at 26° C. and 90% relative humidity for 4-5 days.

The treated egg masses were then assessed to determine the amount of eggs hatched as a percentage of control. The results as set forth below and is based on a rating scale of 1 to 5, said scale is set forth as Example I.

The results of this assessment showed that at a treating dosage of 400 mg/l, each of compounds 1, 2, 3, 4, 5, 6, 19, 20, 23, 27, 28, 29, 31, 32, 33, 41 and 51 gave a scale rating of 1 and each of compounds 22 and 51 gave a scale rating of 3.

In addition, this assessment showed that at a treating dosage of 10 mg/l, each of compounds 3, 4, 6, 23 and 33 gave a scale rating of 1; compound 28 gave a scale rating of 2; each of compounds 27, 31, 32 and 51 gave a scale rating of 3; compound 19 gave a scale rating of 4 and each of compounds 1, 2, 5, 20, 22, 29 and 41 gave a scale rating of 5.

EXAMPLE 4

In this operation, aqueous dispersions were prepared by admixing one of the hereinafter set forth compounds with a predetermined quantity of water and a predetermined amount of a surfactant to give aqueous dispersions containing varying predetermined amounts of one of the compounds as the sole active toxicant. Separate cotton plant leaves were thoroughly wetted briefly with one of the dispersions and the wetted leaves placed in an open petri dish and permitted to dry. After the leaves were dry, 5 live beet armyworm larvae (*Spodoptera exigua*) were placed in each Petri dish. In identical operations, 5 live beet armyworm larvae were placed in control Petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the percent kill and control of the beet armyworm larvae. The percent kill and control is expressed below on a scale of 1 to 5, said scale being set forth in Example I.

The results of this examination showed that at a treating dosage of 400 mg/l, each of compounds 6, 8, 19, 21, 32, 33, 41 and 51 gave a scale rating of 1 and each of compounds 1, 2, 3, 4, 5, 9, 10, 16, 18, 20, 30, 31, 34, 35 and 56 gave a scale rating of 5.

EXAMPLE 5

In this operation, aqueous dispersion were prepared by admixing one of the hereinafter set forth compounds with a predetermined quantity of water and a predetermined amount of a surfactant to give aqueous dispersions of varying predetermined amounts of one of the compounds as the sole active toxicant. Separate 3 inch discs cut from tobacco plant leaves were thoroughly wetted briefly with one of the dispersions and the wetted leaves placed in an open Petri dish and permitted to dry. After the leaves were dry, 5 live tobacco budworm larvae *Heliothis virescens* were placed in each Petri dish. In identical operations, 5 live tobacco budworm larvae were placed in control Petri dishes, the leaf therein having been wetted with a solution containing only water and surfactant. The dishes were maintained under moist conditions conducive for the growth of the tobacco budworm larvae for a period of about 2 days. At the end of the 2-day period, the dishes were examined to determine the percent kill and control of the tobacco budworm larvae. The percent kill and control is expressed below on a scale of 1 to 5, said scale being set forth in Example 1.

The results of this examination showed that at a treating dosage of 400 mg/l, each of compounds 3, 8, 19, 31, 32 and 33 gave a scale rating of 1; each of compounds 4, 6 and 30 gave a scale rating of 2 and each of compounds 1, 2, 5, 9, 10, 16, 18; 20, 22, 23, 26, 34, 35, 41, 51 and 56 gave a scale rating of 5.

EXAMPLE 6

Cotton plants were grown to four true leaves of 7-8 cm diameter. The test compound was prepared as an aqueous/acetone solution or suspension at the required concentration. The foliar parts of the cotton plant were dipped in the test medium for a 10 second period. After drying they were kept in a glasshouse at a temperature of 20° to 25° C. with a minimum photoperiod of 12 hours.

Individual leaves from each treatment were removed and placed in separate 9 cm diameter plastic petri dishes where they were infested with ten, 3rd instar larvae of *Plutella xylostella*. The experimental units were kept in an environmental room at 25° C., 70% humidity with a photoperiod of 16 hours. The leaves in each unit were replaced daily with leaves from plants of the same treatment, i.e., 0, 1, 2 and 3 days.

Assessment was made on the fourth day as a comparison of treated with untreated controls and expressed as a percentage mortality on a scale of 1 to 5 where
1=90-100% mortality
2=75-89% mortality
3=50-74% mortality
4=25-49% mortality and
5=0-24% mortality.

The results of this assessment showed that at a treating dosage of 400 milligrams of the active compound per liter (mg/l), each of compounds 2, 3, 4, 6, 8, 10, 19, 23, 27, 28, 32, 33, 39, 42, 43, 44, 47, 50 and 55 gave a scale rating of 1; compound 41 gave a scale rating of 3 and compound 34 gave a scale rating of 5.

In addition, this assessment showed that at a treating dosage of 10 mg/l, each of compounds 3, 6, 8, 23, 27, 28, 33, 47 and 55 gave a scale rating of 1; each of compounds 10, 19, 39 and 50 gave a scale rating of 2; each of compounds 4, 32 and 44 gave a scale rating of 3; compounds 41 and 43 gave a scale rating of 4 and compounds 2 and 42 gave a scale rating of 5.

The phenylazoanilines employed as starting materials are for the most part known compounds and can be prepared by the techniques taught in the art or by procedures analogous to those taught in the art. In one such procedure, an appropriate aniline corresponding to the formula

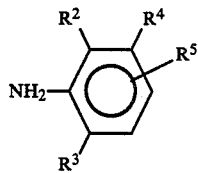

is reacted under acidic conditions at a temperature below 20° C. with (1) a diazotizing agent followed by (2) reacting the thus formed compound with a compound of one of the formulae

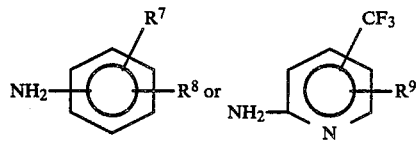

The desired product can be then recovered employing conventional separatory techniques.

EXAMPLE 7

3-Methyl-4-phenylazoaniline

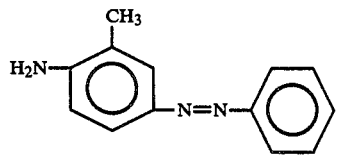

Aniline (11.5 g, 0.124 mol) was dissolved with stirring in a mixture of concentrated hydrochloric acid (30 mls) and water (30 mls) and the resultant solution cooled to 0° C. To this was added a solution of sodium nitrite (8.52 g, 0.123 mol) in water (30 mls), the temperature of the reaction mixture being maintained at <5° C. by the addition of ice. Upon completion of the addition, the mixture was stirred at 0°-5° C. for half an hour.

The cooled solution of benzenediazonium chloride was then added gradually to a cooled (<10° C.), stirred solution of m-toluidine (11.92 g, 0.111 mol) in ethanol (50 mls) and the mixture stirred for two hours at <10° C. It was then filtered, the ochre precipitate washed with water, dried, and recrystallized from petroleum ether (60°-80° C.) to give 3-methyl-4-phenylazoaniline (10.93 g, 46%), m.p. 66°-69° C.

Calculated for $C_{13}H_{13}N_3$: Found: C=73.87; H=6.35; N=19.90. Theory: C=73.91; H=6.20; N=19.89.

By following the above procedure or analogous procedures, the following compounds can be prepared.

TABLE 2

| Compound | M.p. (°C.) | % Found C | H | N | % Calculated C | H | N |
|---|---|---|---|---|---|---|---|
| 3,5-dimethyl-4-phenyl-azoaniline | 67-68 | 74.59 | 6.71 | 18.56 | 74.64 | 6.71 | 18.65 |
| 3,5-dimethyl-4-(3-nitro-phenylazo)aniline | 167-169 | 61.92 | 5.48 | 20.59 | 62.21 | 5.22 | 20.73 |
| 3-methyl-4-(4-nitrophenyl-azo)aniline | 154-156 | 61.08 | 4.66 | 21.83 | 60.93 | 4.72 | 21.86 |
| 3,5-dimethyl-4-(4-nitro-phenylazo)aniline | 159-161 | 62.26 | 5.09 | 20.83 | 62.21 | 5.22 | 20.73 |
| 3-methyl-4-(4-chlorophenyl-azo)aniline | oil | 63.29 | 5.01 | 17.42 | 63.55 | 4.92 | 17.10 |
| 3,5-dimethyl-4-(3,5-dimethylphenylazo)aniline | 93-95 | 76.76 | 6.15 | 16.70 | 76.77 | 6.44 | 16.79 |
| 3,5-dimethyl-4-(4-chloro-3-nitrophenylazo)aniline | | 55.10 | 4.50 | 18.48 | 55.18 | 4.30 | 18.39 |
| 3,5-dimethyl-4-(4-chloro-2-cyanophenylazo)aniline | 170-173 | 63.06 | 4.83 | 20.53 | 63.27 | 4.60 | 19.68 |
| 3-allyloxy-4-phenylazoaniline | | | | | | | |

In another such procedure, an appropriate compound corresponding to one of the formulae

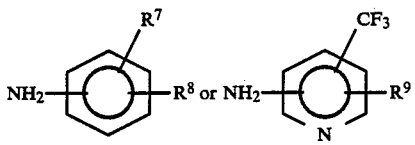

is reacted, under acidic conditions, at a temperature below 20° C. with (1) a diazotizing agent. The reaction product is buffered and then reacted with an aqueous solution of an appropriate substituted anilinomethane sulphonate. The desired product is then separated by conventional separatory procedures.

EXAMPLE 8

3-Chloro-4-(4-nitrophenylazo)aniline

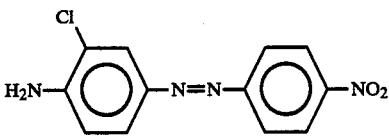

4-Nitroaniline (8.9 g, 0.064 mol) was dissolved with warming in a mixture of concentrated hydrochloric acid (20 mls) and water (20 mls) and the solution poured onto stirred ice (52 g). This was cooled to <5° C. and a solution of sodium nitrite (5 g, 0.072 mol) in water (15 mls) added with stirring, the reaction temperature being maintained at <5° C. This was then stirred at 0°-5° C. for half an hour and sodium acetate trihydrate (20 g) added.

The buffered solution of diazonium salt was added to a vigorously stirred, cooled solution of sodium 3-chloroanilinomethanesulphonate (17.5 g, 0.072 mol) in water (250 mls). The reaction mixture was refrigerated overnight and filtered. The red solid was slurried in 5% sodium hydroxide solution (400 mls) and gradually heated to 95° C. over two hours. This was cooled, filtered, and the solid crystallized from dilute alcohol to give 3-chloro-4-(4-nitrophenylazo)aniline (12.6 g, 71%), m.p. 207°-209° C.

Calculated for $C_{12}H_9ClN_4O_2$: Found: C=52.14; H=3.34; N=20.28. Theory: C=52.09; H=3.29; N=20.25.

Similarly, the following compounds were prepared:

3,5-dimethyl-4-(4-chlorophenylazo)aniline (red oil, 37% of theory).

Calculated for $C_{14}H_{14}ClN_3$: Found: C=64.48; H=5.20; N=16.48. Theory: C=64.74; H=5.43; N=16.18.

4-(4-nitrophenylazo)-3-(1,1,2,2-tetrafluoroethoxy)aniline (red oil, 33% of theory).

Calculated for $C_{14}H_{10}F_4N_4O_3$: Found: C=47.12; H=2.78; N=15.76. Theory: C=46.94; H=2.81; N=15.64.

In another procedure, an appropriate aminoacetanilide is dissolved in a mixture of acetic acid and ethanol and cooled to a temperature below 20° C. and reacted with an appropriate nitrosobenzene. The corresponding phenylazoacetoanilide thus formed is treated with an alkali hydroxide to form the desired compound.

EXAMPLE 9

3-Phenylazoaniline

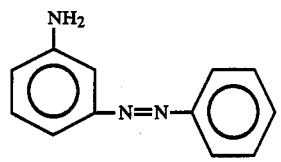

3-Aminoacetanilide (10 g, 0.067 mol) was dissolved in a mixture of acetic acid (12 mls) and ethanol (64 mls) and cooled to 5° C. To this was added a cooled (5° C.) solution of nitrosobenzene (7.65 g, 0.071 mol) in ethanol (50 mls) with stirring. This was stirred at 5° C. for two hours, allowed to warm to room temperature and poured into water (100 mls). This was then filtered, the black solid dried, and purified by chromatography (silica gel:dichloromethane) and recrystallization from benzene:petroleum ether (80:100) to give 3-phenylazoacetanilide (8.33 g, 53%) m.p.=133°-134° C.

This solid (5 g, 0.021 mol) was heated under reflux with potassium hydroxide (2.95 g, 0.053 mol) in water (5 mls) and ethanol (50 mls) to give, after work-up, 3-phenylazoaniline (3.7 g, 89%), m.p.=54°-56° C.

In a similar manner, 5-amino-2-fluoroacetanilide was condensed with nitrosobenzene to give 2-fluoro-5-phenylazoacetanilide in 17% yield, m.p.=165°-166° C.

Calculated for $C_{14}H_{12}FN_3O$: Found: C=65.27; H=4.70; N=16.32. Theory: C=65.36; H=4.70; N=16.33.

This was then hydrolyzed with potassium hydroxide in aqueus methanol to give 2-fluoro-5-phenylazoaniline in quantitative yield which was used without further purification.

We claim:

1. A method for killing and controlling insects which comprises applying to the insect and/or its habitat an insecticidal amount of a compound of the general formula

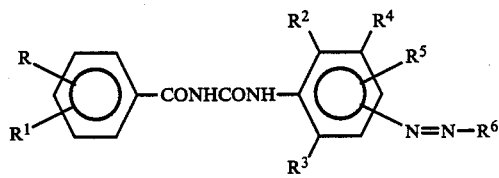

wherein R and $R^1$ are each independently a hydrogen or halogen atom, a $C_1$-$C_4$ alkyl or a $C_1$-$C_4$ haloalkyl group; $R^2$ and $R^3$ are each independently a hydrogen or halogen atom or a $C_1$-$C_4$ alkyl group; $R^4$ and $R^5$ are each independently a hydrogen or halogen atom, or $C_1$-$C_4$ alkyl, $C_1$-$C_4$ haloalkyl, $C_1$-$C_4$ alkoxy, $C_1$-$C_4$ haloalkoxy, $C_2$-$C_4$ alkenyl, $C_2$-$C_4$ haloalkenyl, $C_2$-$C_4$ alkenyloxy, $C_2$-$C_4$ haloalkenyloxy or a $C_2$-$C_4$ alkynyl group; $R^6$ is

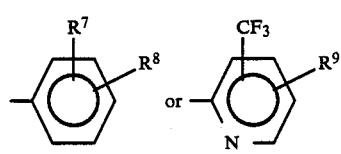

wherein $R^7$ and $R^8$ are each independently a hydrogen or halogen atom, or a nitro, $C_1$-$C_4$ alkyl, $C_1$-$C_4$ haloalkyl or cyano group and $R^9$ is a halogen atom or a $C_1$-$C_4$ alkyl or a $C_1$-$C_4$ haloalkyl group in intimate admixture with an inert carrier therefor.

* * * * *